United States Patent [19]
Oblong et al.

[11] Patent Number: 5,939,082
[45] Date of Patent: *Aug. 17, 1999

[54] METHODS OF REGULATING SKIN APPEARANCE WITH VITAMIN $B_3$ COMPOUND

[75] Inventors: John Erich Oblong, Cincinnati; Donald Lynn Bissett, Hamilton; Kimberly Ann Biedermann, Cincinnati, all of Ohio

[73] Assignee: The Procter & Gamble Company, Cincinnati, Ohio

[ * ] Notice: This patent is subject to a terminal disclaimer.

[21] Appl. No.: 08/834,010

[22] Filed: Apr. 11, 1997

Related U.S. Application Data

[63] Continuation-in-part of application No. 08/554,067, Nov. 6, 1995, Pat. No. 5,833,998
[60] Provisional application No. 60/016,043, Apr. 23, 1996, provisional application No. 60/025,242, Sep. 16, 1996, and provisional application No. 60/028,902, Oct. 21, 1996.

[51] Int. Cl.$^6$ .................................................... A61K 7/48
[52] U.S. Cl. ........................ 424/401; 514/844; 514/845; 514/846; 514/938
[58] Field of Search ........................... 424/401; 514/844, 514/845, 846, 938

[56] References Cited

U.S. PATENT DOCUMENTS

| | | | |
|---|---|---|---|
| 4,938,960 | 7/1990 | Ismail | 424/195.1 |
| 5,254,331 | 10/1993 | Mauser | 424/59 |
| 5,520,919 | 5/1996 | Lerner | 424/401 |
| 5,545,399 | 8/1996 | Lee et al. | 424/59 |

FOREIGN PATENT DOCUMENTS

| | | | |
|---|---|---|---|
| 0 512814A1 | 11/1992 | European Pat. Off. | A61K 7/48 |
| 2242553 | 3/1974 | Germany . | |
| 63-060910 | 3/1988 | Japan | A61K 7/00 |
| 8-073338 | 3/1996 | Japan | A61K 7/48 |
| WO 91/14431 | 10/1991 | WIPO . | |
| WO 94/09756 | 5/1994 | WIPO | A61K 7/48 |

OTHER PUBLICATIONS

Database WPI, Week 9011, Derwent Publications Ltd., London, GB; AN 90–079175, Feb. 1, 1990.

Tay et al., "Stimulation of Collagen Type I and Type III mRNA Synthesis in Human Skin Fibroblasts by Nicotinamide", *Clinical Research*, vol. 39, No. 1, 1991.

Commerical product information: Chanel Complexe Intensif Night Lift Cream.

Commerical product information: Chanel Creme Parfaite Night Lift Plus Multi–Hydroxy.

*Primary Examiner*—Jyothsna Venkat
*Attorney, Agent, or Firm*—Darryl C. Little; George W. Allen

[57] ABSTRACT

The present invention relates to topical compositions comprising a vitamin $B_3$ compound which are useful for regulating skin condition, especially for regulating the signs of skin aging.

5 Claims, No Drawings

METHODS OF REGULATING SKIN APPEARANCE WITH VITAMIN $B_3$ COMPOUND

CROSS REFERENCE

This application claims priority under Title 35, United States Code 119(e) from Provisional Application Ser. No. 60/016,043, filed Apr. 23, 1996, Provisional Application Serial No. 60/025,242, filed Sep. 16, 1996, and Provisional Application Serial No. 60/028,902, filed Oct. 21, 1996. This application is a continuation-in-part of U.S. application Ser. No. 08/554,067, filed Nov. 6, 1995 now U.S. Pat. No. 5,833,998.

TECHNICAL FIELD

The present invention relates to topical compositions containing a vitamin $B_3$ compound for regulating the condition of skin, especially for regulating visible and/or tactile discontinuities in skin associated, e.g., with skin aging. Preferred compositions contain niacinamide.

BACKGROUND OF THE INVENTION

Many personal care products currently available to consumers are directed primarily to improving the health and/or physical appearance of the skin. Among these skin care products, many are directed to delaying, minimizing or even eliminating skin wrinkling and other histological changes typically associated with the aging of skin or environmental damage to human skin.

Skin is subject to insults by many extrinsic and intrinsic factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin. Whether extrinsic or intrinsic, these factors result in visible signs of skin aging and environmental damage, such as wrinkling and other forms of roughness (including increased pore size, flaking and skin lines), and other histological changes associated with skin aging or damage. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Extrinsic or intrinsic factors may result in the thinning and general degradation of the skin. For example, as the skin naturally ages, there is a reduction in the cells and blood vessels that supply the skin. There is also a flattening of the dermal-epidermal junction which results in weaker mechanical resistance of this junction. See, for example, Oikarinen, "The Aging of Skin: Chronoaging Versus Photoaging," *Photodermatol. Photoimmunol. Photomed.*, vol. 7, pp. 3–4, 1990, which is incorporated by reference herein in its entirety.

It has now been found that vitamin $B_3$ compounds, including niacinamide, provide benefits in regulating skin condition previously unrecognized in the art of which the present inventors are aware. For example, topical niacinamide can regulate the signs of skin aging, e.g., reduce or efface the visibility of the fine lines, wrinkles, and other forms of uneven or rough surface texture associated with aged or photodamaged skin. It has also now been found that topical compositions containing a vitamin $B_3$ compound and a retinoid provide benefits in regulating skin condition previously unrecognized in the art of which the present inventors are aware. For example, such compositions enable the regulation of signs of skin aging with decreased potential for retinoid dermatitis. In addition, the vitamin $B_3$ compound in combination with certain retinoids synergistically regulates signs of skin aging, especially visible and/or tactile discontinuities in skin texture associated with aged skin, including fine lines and wrinkles.

It is therefore an object of the present invention to provide topical compositions for prophylactically and/or therapeutically regulating mammalian skin condition (especially of human skin, more especially facial skin), containing a vitamin $B_3$ compound, especially niacinamide.

It is another object of the present invention to provide topical compositions for prophylactically and/or therapeutically regulating signs of mammalian skin aging, containing a vitamin $B_3$ compound, especially niacinamide.

It is another object of the present invention to provide topical compositions for prophylactically and/or therapeutically regulating visible and/or tactile discontinuities in mammalian skin texture, including fine lines, wrinkles, enlarged pores, roughness and other skin texture discontinuities associated with aged skin, containing a vitamin $B_3$ compound, especially niacinamide.

Other objects of the present invention are to provide such topical compositions further comprising a retinoid.

The present invention also relates to methods of providing such regulation using the subject compositions.

These and other objects of this invention will become apparent in light of the following disclosure.

SUMMARY OF THE INVENTION

The present invention relates to regulation of skin condition involving the topical application of a composition containing a vitamin $B_3$ compound, especially niacinamide. The present invention also relates to regulation of skin condition involving topical application of a composition containing a vitamin $B_3$ compound, especially niacinamide, and a retinoid. The invention especially relates to regulation of signs of skin aging, more especially regulating visible and/or tactile discontinuities in mammalian skin texture, including discontinuities associated with aged skin, involving the topical application of such compositions. The present invention relates to both prophylactic and therapeutic regulation of skin condition.

In preferred embodiments, the vitamin $B_3$ compound is substantially free of the salt form and is uncomplexed, the vitamin $B_3$ compound is niacinamide, and the carrier contains a hydrophilic diluent.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

The compositions of the present invention are useful for topical application and for regulating skin condition, including visible and/or tactile discontinuities in skin (especially the skin surface; such discontinuities are generally undesired). Such discontinuities may be induced or caused by internal and/or external factors, and include the signs of skin aging described herein. "Regulating skin condition" includes prophylactically regulating and/or therapeutically regulating skin condition, including visible and/or tactile discontinuities in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

The compositions of the present invention are useful for regulating signs of skin aging, more especially visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for therapeutically regulating visible and/or tactile discontinuities in mammalian skin texture, including texture discontinuities associated with skin aging. As used herein, therapeutically regulating such discontinuities includes ameliorating, e.g., diminishing, minimizing and/or effacing visible and/or tactile discontinuities in the texture of mammalian skin, to thereby provide improved skin appearance and/or feel, e.g., a smoother, more even appearance and/or feel. Such visible and/or tactile discontinuities in skin texture include crevices, bumps, pores, fine lines, wrinkles, scales, flakes and/or other forms of textural unevenness or roughness associated with skin aging. For example, the length, depth, and/or other dimension of lines and/or wrinkles are decreased, the apparent diameter of pores decreases, or the apparent height of tissue immediately proximate to pore openings approaches that of the interadnexal skin.

The present invention is also especially useful for prophylactically regulating visible and/or tactile discontinuities in mammalian skin texture, including texture discontinuities associated with skin aging. As used herein, prophylactically regulating such discontinuities includes delaying, minimizing and/or preventing visible and/or tactile discontinuities in the texture of mammalian skin, to thereby provide improved skin appearance and/or feel, e.g., a smoother, more even appearance and/or feel.

The compositions of the present invention are also useful for promoting exfoliation of the skin. Without intending to be bound or limited by theory, it is believed that the compositions containing the vitamin $B_3$ compound, particularly niacinamide, strengthen the energy state of cells regulating exfoliation, resulting in normalization of epidermal differentiation and keratinization.

Vitamin $B_3$ Component

The compositions of the present invention comprise a safe and effective amount of a vitamin $B_3$ compound. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

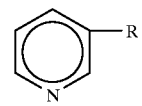

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid ($C_8H_8N_2O_3$) and nicotinyl hydroxamic acid ($C_6H_6N_2O_2$), which have the following chemical structures:

nicotinuric acid:

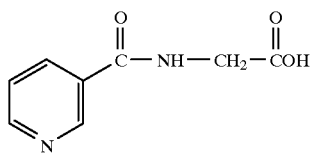

nicotinyl hydroxamic acid:

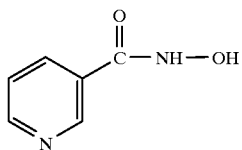

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methylnicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Iosascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

Carrier

The compositions of the present invention comprise a dermatologically acceptable carrier within which the vitamin $B_3$ compound is incorporated to enable the vitamin $B_3$ compound and optional other actives to be delivered to the skin at an appropriate concentration. The carrier can thus act as a diluent, dispersant, solvent, or the like for the active(s) which ensures that it can be applied to and distributed evenly over the selected target at an appropriate concentration.

The carrier may contain one or more dermatologically acceptable solid, semi-solid or liquid fillers, diluents, solvents, extenders and the like. The carrier may be solid, semi-solid or liquid. The carrier can itself be inert or it can possess dermatological benefits of its own. Concentrations of the carrier can vary with the carrier selected and the intended concentrations of the essential and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction which would substantially reduce the efficacy of the composition under ordinary use situations.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes.

Preferred carriers contain a dermatologically acceptable, hydrophilic diluent. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Water is a preferred diluent. The composition preferably comprises from about 80% to about 99.99% of the hydrophilic diluent and the vitamin $B_3$ compound in the above described amounts.

Solutions according to the subject invention typically include a dermatologically acceptable hydrophilic diluent. Solutions useful in the subject invention preferably contain from about 80% to about 99.99% of the hydrophilic diluent and the vitamin $B_3$ compound in the above described amounts.

Aerosols according to the subject invention can be formed by adding a propellant to a solution such as described above. Exemplary propellants include chloro-fluorinated lower molecular weight hydrocarbons. Additional propellants that are useful herein are described in Sagarin, *Cosmetics Science and Technology*, 2nd Edition, Vol. 2, pp. 443–465 (1972), incorporated herein by reference. Aerosols are typically applied to the skin as a spray-on product.

Preferred carriers comprise an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Preferred vitamin $B_3$ compounds distribute primarily into the aqueous phase. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317–324 (1986), each incorporated herein by reference.

The emulsion may also contain an anti-foaming agent to minimize foaming upon application to the skin. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less.

Preferred water-in-silicone and oil-in-water emulsions are described in greater detail below.

a) Water-in-silicone Emulsion

Water-in-silicone emulsions contain a continuous silicone phase and a dispersed aqueous phase.

(i) Continuous Silicone Phase

Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the optional retinoid. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in copending U.S. patent application Ser. No. 08/570,275, filed Dec. 11, 1995, in the names of Joseph Michael Zukowski, Brent William Mason, Larry Richard Robinson and Greg George Hillebrand, incorporated herein by reference.

The organopolysiloxane oil for use in the composition may be volatile, nonvolatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_{x}SiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217° C., which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_3)_3SiO_{1/2}]_x[SiO_2]_y$, wherein x is an *integer from about* 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc..

(ii) Dispersed Aqueous Phase

The topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 80%, more preferably from about 60% to about 80%, water in the dispersed aqueous phase by weight of the composition.

(iii) Emulsifier for Dispersing the Aqueous Phase

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2–C30 pendant side chains. Still other useful dimethicone copolyols include materials having various cationic, anionic, amphoteric, and zwitterionic pendant moieties.

The dimethicone copolyol emulsifiers useful herein can be described by the following general structure:

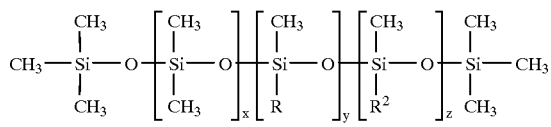

wherein R is C1–C30 straight, branched, or cyclic alkyl and $R^2$ is selected from the group consisting of
—$(CH_2)_n$—O—$(CH_2CHR^3O)_m$—H,
and
—$(CH_2)_n$—O—$(CH_2CHR^3O)_m$—$(CH_2CHR^4O)_o$—H,
wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:
—$(CH_2)_n$—O—$R^5$,
wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemthicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary,* Fifth Edition, 1993, which is incorporated by reference herein in its entirety.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries* vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology,* 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science,* 12, 135–139 (1990); and D. G. Krzysik et al., "A New Silicone Emulsifier For Water-in-Oil Systems," *Drug and Cosmetic Industry,* vol. 146(4) pp. 28–81 (April 1990); incorporated by reference herein in their entirety.

Among the non-silicon-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers,* North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these references are incorporated herein by reference in their entirety.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

b) Oil-in-Water Emulsions

Other preferred topical carriers include oil-in-water emulsions, having a continuous aqueous phase and a hydrophobic, water-insoluble phase ("oil phase") dispersed therein. An especially preferred oil-in-water emulsion, containing a structuring agent, hydrophilic surfactant and water, is described in detail hereinafter.

(i) Structuring Agent

A preferred oil-in-water emulsion comprises a structuring agent to assist in the formation of a liquid crystalline gel network structure. Concentrations of such structuring agents are from about 1% to about 20%, preferably from about 1% to about 10%, more preferably from about 3% to about 9% by weight of the topical carrier.

Suitable structuring agents are those selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.

Preferred structuring agents include stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof. Most preferred is steareth-2, available under the tradename of Brij® 72 from ICI Americas.

(ii) Hydrophilic Surfactant

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Suitable surfactants include any of a wide variety of known cationic, anionic, zwitterionic, and amphoteric surfactants. See McCutcheon's, *Detergents and Emulsifiers,* North American Edition (1986), published by Allured Publishing Corporation; U.S. Pat. Nos. 5,011,681; 4,421,769; and 3,755,560; these references are incorporated herein by reference in their entirety.

The exact surfactant chosen will depend upon the pH of the composition and the other components present.

Preferred are cationic surfactants, especially dialkyl quaternary ammonium compounds, examples of which are described in U.S. Pat. Nos. 5,151,209; 5,151,210; 5,120,532; 4,387,090; 3,155,591; 3,929,678; 3,959,461; McCutcheon's, *Detergents & Emulsifiers,* (North American edition 1979) M.C. Publishing Co.; and Schwartz, et al., *Surface Active Agents, Their Chemistry and Technology,* New York: Interscience Publishers, 1949; which descriptions are incorporated herein by reference. The cationic surfactants useful herein include cationic ammonium salts such as those having the formula:

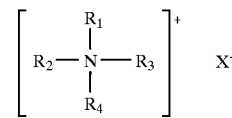

wherein $R_1$, is an alkyl group having from about 12 to about 30 carbon atoms, or an aromatic, aryl or alkaryl group having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH$—$(CH_2)_n$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$R_1$—SO$_3$—M wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas RN[(CH$_2$)$_m$CO$_2$M]$_2$ and RNH(CH$_2$)$_m$CO$_2$M wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(iii) Water

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics Science and Technology*, 2nd Edition, Vol. 1, pp. 32–43 (1972), incorporated herein by reference, contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and the vitamin $B_3$ compound in the above described amounts. A cream typically comprises from about 5% to about 50%, preferably from about 10% to about 20%, of emollient; from about 45% to about 85%, preferably from about 50% to about 75%, water; and the vitamin $B_3$ compound in the above described amounts.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology*, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and the vitamin $B_3$ compound in the above described amount.

Compositions of this invention useful for cleansing ("cleansers") are formulated with a suitable carrier, e.g., as described above, and preferably contain, in addition to the vitamin $B_3$ compound in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers*, North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery sytems, see U.S. Pat. No. 4,835,148, Barford et al., issued May 30, 1989, incorporated herein by reference in its entirety.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for the vitamin $B_3$ compound and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

The compositions of the present invention are preferably formulated to have a pH of 10.5 or below. The pH values of these compositions preferably range from about 2 to about 10.5, more preferably from about 3 to about 8, even more preferably from about 4 to about 7, and also from about 4.5 to about 5.5.

Optional Components

The topical compositions of the present invention may comprise a wide variety of optional components, provided that such optional components are physically and chemically compatible with the essential components described herein, and do not unduly impair stability, efficacy or other use benefits associated with the compositions of the present invention. Any optional ingredients should be compatible with the vitamin $B_3$ compound such that its activity does not decrease unacceptably, preferably not to any significant extent, over a useful period (preferably at least about two years under normal storage conditions). For example, strong oxidizing agents may be incompatible with the vitamin $B_3$ compound such that such agents are preferably avoided. Optional components may be dispersed, dissolved or the like in the carrier of the present compositions.

Optional components include aesthetic agents and other active agents. For example, the compositions may include absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in *Harry's Cosmeticology,* 7th Ed., Harry & Wilkinson (Hill Publishers, London 1982); in *Pharmaceutical Dosage Forms-Disperse Systems;* Lieberman, Rieger & Banker, Vols. 1 (1988) & 2 (1989); Marcel Decker, Inc.; in *The Chemistry and Manufacture of Cosmetics.* 2nd. Ed., deNavarre (Van Nostrand 1962–1965); and in *The Handbook of Cosmetic Science and Technology* 1st Ed.. Knowlton & Pearce (Elsevier 1993).

It has been found that certain compounds may negatively impact the skin appearance benefits otherwise provided by the vitamin $B_3$ compound. Such compounds include ascorbic acid and N-acetyl cysteine. Without intending to be bound or limited by theory, it is believed that these compounds may form large complexes, e.g., salts, with the vitamin $B_3$ compound which reduce the availability of the vitamin $B_3$ compound to the skin. Such complexes are believed to have a relatively high molecular weight which decreases their availability to the skin. Therefore, in one embodiment of the invention, the compositions do not contain these compounds or compounds which are capable of forming similarly large complexes with the vitamin $B_3$ compound. In another embodiment, where the composition contains these compounds or compounds which are capable of forming large complexes with the vitamin $B_3$ compound, one or more of the approaches previously described herein for minimizing or preventing the formation of undesirable complexes are preferred.

For example, the impact of such compounds on the efficacy of the vitamin $B_3$ compound decreases with a decrease in pH such that pH adjustments can be employed to minimize or obviate such effects. For example, when the composition contains N-acetyl-L-cysteine, the pH of the composition is preferably adjusted to from about 2 to about 5, more preferably from about 3 to about 4. The adjustment of pH to obviate substantial impacts on efficacy is well within the level of ordinary skill in the art.

Specific examples of optional components include the following. The active ingredients useful herein are categorized by their cosmetic and/or therapeutic benefit or their postulated mode of action. However, it is to be understood that the active ingredients useful herein can in some instances provide more than one cosmetic and/or therapeutic benefit or operate via more than one mode of action. Therefore, classifications herein are made for the sake of convenience and are not intended to limit the active ingredient to that particular application or applications listed.

A. Anti-Inflammatory Agents

A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology* 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, etofenamate, aspirin and flufenamic acid are most preferred.

Finally, so-called "natural" anti-inflammatory agents are useful in methods of the subject invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), kola extract, chamomile, and sea whip extract, may be used. Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

B. Retinoids

In a preferred embodiment, the compositions of the present invention also contain a retinoid. The vitamin $B_3$ compound and retinoid provide unexpected benefits in regulating skin condition, especially in therapeutically regulating signs of skin aging, more especially wrinkles, lines, and pores. Without intending to be bound or otherwise limited by theory, it is believed that the vitamin $B_3$ compound increases the conversion of certain retinoids to trans-retinoic acid, which is believed to be the biologically active form of the retinoid, to provide synergistic regulation of skin condition (namely, increased conversion for retinol, retinol esters, and retinal). In addition, the vitamin $B_3$ compound unexpectedly mitigates redness, inflammation, dermatitis and the like which may otherwise be associated with topical application of retinoid (often referred to, and hereinafter alternatively referred to as "retinoid dermatitis"). Furthermore, the combined vitamin $B_3$ compound and retinoid tend to increase the amount and activity of thioredoxin, which tends to increase collagen expression levels via the protein AP-1. Therefore, the present invention enables reduced active levels, and therefore reduced potential for retinoid dermatitis, while retaining significant positive skin conditioning benefits. In addition, higher levels of retinoid may still be used to obtain greater skin conditioning efficacy, without undesirable retinoid dermatitis occurring.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and Reissue 34,075, issued Sep. 22, 1992 to Purcell et al.. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl proprionate, retinal and combinations thereof. More preferred are retinol and retinyl palmitate.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate [tocopherol ester of retinoic acid (trans- or cis), adapalene {6-[3-(1-adamantyl)-4-methoxyphenyl]-2-naphthoic acid}, and tazarotene are most preferably used in an amount of from or about 0.01% to or about 2%. When the composition contains a retinoid, the vitamin $B_3$ compound is preferably used in an amount of from or about 0.1% to or about 10%, more preferably from or about 2% to or about 5%.

C. Antimicrobial Agents

As used herein, "antimicrobial agent" means a compound capable of destroying microbes, preventing the development of microbes or preventing the pathogenic action of microbes. Antimicrobial agents are useful, for example, in controlling acne. A safe and effective amount of an antimicrobial agent may be added to compositions of the subject invention, preferably from about 0.001% to about 10%, more preferably from about 0.01% to about 5%, also from about 0.05% to about 2% or from about 0.05% to about 1% of the compositions. Preferred antimicrobial agents useful in the subject invention are benzoyl peroxide, erythromycin, tetracycline, clindamycin, azelaic acid, and sulfur resorcinol.

D. Antiandrogens

As used herein, "anti-androgen" means a compound capable of correcting androgen-related disorders by interfering with the action of androgens at their target organs. The target organ for the subject invention is mammalian skin. Exemplary antiandrogens include pregnenalone (and its derivatives), hops extract, oxygenated alkyl substituted bicyclo alkanes (e.g., ethoxyhexyl-bicyclo octanones such as marketed by Chantal Pharmaceutical of Los Angeles, Calif. under the trade names ETHOCYN and CYOCTOL, and 2-(5-ethoxy hept-1-yl)bicylo[3.3.0]octanone), and oleanolic acid. Suitable antiandrogens are disclosed in U.S. Pat. Nos. 4,689,345 and 4,855,322, both issued to Kasha et al. on Aug. 25, 1987 and Aug. 8, 1989, respectively, each incorporated herein by reference.

Sunscreens and Sunblocks

Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy4-methoxybenzophenone, octyldimethyl-p-aminobenzoic acid, digalloyltrioleate, 2,2-dihydroxy-4-methoxybenzophenone, ethyl4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or arinobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreens useful in the compositions useful in the subject invention are 2-ethylhexyl-p-methoxycinnamate, butylmethoxydibenzoyl-methane, 2-hydroxy4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)4-aminobenzoic acid ester of 2-hydroxy4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Suitable inorganic sunscreens or sunblocks include metal oxides, e.g., zinc oxide and titanium dioxide. For example, the use of a titanium dioxide in topical sunscreen compositions that is applicable to the present invention is described in copending application Ser. No. 08/448,942, filed on May 24, 1995, in the names of Jiang Yue, Lisa R. Dew and Donald L. Bissett, incorporated herein by reference.

Especially preferred sunscreens or sunblocks include the metal oxides such as zinc oxide and titanium dioxide, butylmethoxydibenzoylmethane, 2-ethylhexyl-p-methoxycinnamate, phenyl benzimidazole sulfonic acid, and octocrylene.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

Preferred compositions of the subject invention include an anti-oxidant/radical scavenger as an active in addition to the primary active agents. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

G. Chelators

As used herein, "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995; all incorporated herein by reference. Preferred chelators useful in compositions of the subject invention are furildioxime and derivatives thereof.

H. Organic Hydroxy Acids

Compositions of the present invention preferably comprise an organic hydroxy acid. Suitable hydroxy acids include $C_1$–$C_{18}$ hydroxy acids, preferably $C_8$ or below. The hydroxy acids can be substituted or unsubstituted, straight chain, branched chain or cyclic (preferably straight chain), and saturated or unsaturated (mono- or poly-unsaturated) (preferably saturated). Non-limiting examples of suitable hydroxy acids include salicylic acid, glycolic acid, lactic acid, 5 octanoyl salicylic acid, hydroxyoctanoic acid, hydroxycaprylic acid, and lanolin fatty acids. Preferred concentrations of the organic hydroxy acid range from about 0.1% to about 10%, more preferably from about 0.2% to about 5%, also preferably from about 0.5% to about 2%. Salicylic acid is preferred. The organic hydroxy acids enhance the skin appearance benefits of the present invention. For example, the organic hydroxy acids tend to improve the texture of the skin.

I. Desquamation Agents/Exfoliants

A safe and effective amount of a desquamation agent is preferably added to the compositions of the subject invention, more preferably from about 0.1% to about 10%, even more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises sulfhydryl compounds and zwitterionic surfactants and is described in copending application Ser. No. 08/480,632, filed on Jun. 7, 1995 in the name of Donald L. Bissett, corresponding to PCT Application No. U.S. 95/08136, filed Jun. 29, 1995, each incorporated herein by reference. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCT Application No. 94/12745, filed Nov. 4, 1994, published May 18, 1995, each incorporated herein by reference. Zwitterionic surfactants such as described in these applications are also useful as desquamatory agents herein, with cetyl betaine being particularly preferred.

J. Depilation Agents

The compositions of the present invention may include a safe and effective amount of a depilation agent. When used, the composition preferably contains from about 0.1% to about 10%, more preferably from about 0.2% to about 5%, also preferably from about 0.5% to about 2% of depilation agent. A depilation agent preferred for use herein comprises a sulfhydryl compound, e.g., N-acetyl-L-cysteine. The use of such depilation agents is described in more detail in copending application Ser. No. 08/479,878, filed on Jun. 7, 1995, in the name of Greg G. Hillebrand and Vladimir Gartstein, corresponding to PCT Application No. U.S. 95/07311, filed Jun. 8, 1995, each incorporated herein by reference.

K. Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate. Skin lightening agents suitable for use herein also include those described in copending patent application Ser. No. 08/479, 935, filed on Jun. 7, 1995 in the name of Hillebrand, corresponding to PCT Application No. U.S. 95/07432, filed Jun. 12, 1995; and copending patent application Ser. No.08/ 390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995; all incorporated herein by reference.

L. Zinc Salts

The compositions of the present invention may further comprise a zinc salt. Zinc salts are especially preferred where the composition contains a sulfhydryl compound, e.g., N-acetyl-L-cysteine. Without intending to be limited or bound by theory, it is believed that the zinc salt acts as a chelating agent capable of complexing with the sulfhydryl compound prior to topical application, stabilizes the sulfhydryl compound and/or controls odor associated with the sulfhydryl compound.

Concentrations of the zinc salt can range from about 0.001% to about 10%, more preferably from about 0.01% to about 5%, most preferably from about 0.1% to about 0.5% by weight of the composition.

Preferred zinc salts include zinc acetate, zinc acetate hydrates such as zinc acetate-2-water, zinc aluminum oxide complexes such as gahnite, zinc diamine, zinc antimonide, zinc bromate hydrates such as zinc bromate-6-water, zinc bromide, zinc carbonates such as zincspar and smithsonite, zinc chlorate hydrates such as zinc chlorate-4-water, zinc chloride, zinc diamine dichloride, zinc citrate, zinc chromate, zinc dichromate, zinc diphosphate, zinc hexacyanofluoride ferrate (II), zinc fluoride, zinc fluoride hydrates such as zinc fluoride-4-water, zinc formate, zinc formate hydrates such as zinc formate-2-water, zinc hydroxide, zinc iodate, zinc iodate hydrates such as zinc iodate-2-water, zinc iodide, zinc iron oxide complexes, zinc nitrate hydrates such as zinc nitrate-6-water, zinc nitride, zinc oxalate hydrates such as zinc oxalate-2-water, zinc oxides such as zincite, zinc perchlorate hydrates such as zinc perchlorate-6-water, zinc permanganate hydrates such as zinc permanganate-6-water, zinc peroxide, zinc p-phenolsulfonate hydrates such as zinc p-phenosulfonate-8-water, zinc phosphate, zinc phosphate hydrates such as zinc phosphate-4-water, zinc phosphide, zinc propionate, zinc selenate hydrates such as zinc selenate-5-water, zinc selenide, zinc silicates such as zinc silicate (2) and zinc silicate (4), zinc silicon oxide water complexes such as hemimorphite, zinc hexafluorosilicate hydrates such as zinc hexafluorosilicate-6-water, zinc stearate, zinc sulfate, zinc sulfate hydrates such as zinc sulfate-7-water, zinc sulfide, zinc sulfite hydrates such as zinc sulfite-2-water, zinc telluride, zinc thiocyanate, zinc (II) salts of N-acetyl L-cysteine, and mixtures thereof.

Especially preferred zinc salts include zinc citrate, zinc oxide, zinc chloride, zinc acetate, zinc stearate, zinc sulfate, and mixtures thereof. Zinc citrate is especially preferred.

M. Humectants, Moisturizers, and Skin Conditioners

The compositions of the present invention may further comprise a humectant, moisturizing agent or other skin conditioning agent. A variety of these materials can be employed and each can be present at a level of from or about 0.1% to or about 20%, more preferably from or about 1% to or about 10%, and most preferably from or about 2% to or about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also useful herein are the propoxylated glycerols described in U.S. Pat. No. 4,976,953, which is description is incorporated herein by reference.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

N. Other Optional Components

The compositions of the present invention may also include an extract obtained by suitable physical and/or chemical isolation from natural sources (e.g., plants, fungi, by-products of microorganisms), including those known in the topical personal care art. Preferred extracts are those which enhance the skin appearance benefits of the present invention, and which are preferably used in a safe and effective amount, more preferably an amount of from 0.1% to about 20%, even more preferably 0.5% to about 10%, also from 1% to about 5%. Such extracts include plant and fungal extracts such as extracts of yeast, rice bran, and of the plant Centella Asiatica. Natural extracts of Centella Asiatica are preferred and are commercially available from MMP, Inc. of Plainfield, N.J. under the trade name(s) Centella Asiatica E.P.C.A. ("Extract Purified of *Centella asiatica*") and *Genines amel. Genines amel* is the purer form of the extract.

Compounds which are known to stimulate the production of collagen can also be used in the present invention. Such compounds include Factor X (kinetin), Factor Z (zeatin), n-methyl taurine, dipalmitoyl hydroxyproline, palmitoyl hydroxy wheat protein, biopeptide CL (palmitoyl glycyl-histidyl-lysine), ASC III (Amplifier of Synthesis of Collagen III, E. Merck, Germany), and beta glucan.

The compositions hereof can also include natural ceramides or the like, for example, ceramide 1-6.

The compositions can also contain an oil absorbent such as are known in the art, e.g. clays (e.g. bentonite) and polymeric absorbents (e.g., MICROSPONGES 5647 and POLYTRAP, both commercially available from Advanced Polymer Systems, Inc. of Redwood City, Calif., USA.. MICROSPONGES 5647 is a polymer mixture derived from styrene, methyl methacrylate, and hydrogel acrylate/methacrylate.

Other examples of additional components useful herein include the following: water-soluble vitamins and derivatives thereof [e.g., vitamin C]; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220). Also useful are crosslinked and non-crosslinked nonionic and cationic polyacrylamides [e.g., Salcare SC92 which has the CTFA designation polyquaternium 32 (and) mineral oil, and Salcare SC 95 which has the CTFA designation polyquaternium 37 (and) mineral oil (and) PPG-1 trideceth-6, and the nonionic Seppi-Gel polyacrylamides available from Seppic Corp.]. Also useful are crosslinked and uncrosslinked carboxylic acid polymers and copolymers such as those containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (examples useful herein include the carbomers, which are homopolymers of acrylic acid crosslinked with allyl ethers of sucrose or pentaerytritol and which are available as the Carbopol® 900 series from B.F. Goodrich, and copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol, these copolymers being known as acrylates/C10–30 alkyl acrylate crosspolymers and are commercially available as Carbopol® 1342, Pemulen TR-1, and Pemulen TR-2, from B.F. Goodrich). These carboxylic acid polymers and copolymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary*, fourth edition, 1991, pp. 12 and 80; which is also incorporated herein by reference.

Also useful herein are aesthetic components such as fragrances, pigments, colorings, essential oils, skin sensates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate and the like.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present invention are useful for regulating mammalian skin condition (especially human skin, more especially human facial skin), including visible and/or tactile discontinuities in skin, signs of skin aging, and visible and/or tactile discontinuities in skin associated with skin aging (including fine lines, wrinkles, large pores, surface roughness and other texture discontinuities associated with aged skin). Such regulation includes prophylactic and therapeutic regulation.

Regulating skin condition involves topically applying to the skin a safe and effective amount of a composition of the present invention. The amount of the composition which is applied, the frequency of application and the period of use will vary widely depending upon the level of vitamin $B_3$ compound and/or other components of a given composition and the level of regulation desired, e.g., in light of the level of skin aging present in the subject and the rate of further skin aging.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 2 mg/$cm^2$.

Regulating skin condition is preferably practiced by applying a composition in the form of a skin lotion, cream, cosmetic, or the like which is intended to be left on the skin for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A skin cream is prepared by conventional methods from the following components.

|  | Ingredient (CTFA Name) | Weight % |
|---|---|---|
| PHASE A: | Water U.S.P. | 57.31 |
|  | Disodium EDTA | 0.13 |
|  | Methyl Paraben | 0.25 |
|  | Glycerin | 3.00 |
|  | Zinc Citrate | 1.00 |
| PHASE B: | Cetyl Alcohol | 0.56 |
|  | Stearyl Alcohol | 2.03 |
|  | Behenyl Alcohol | 0.22 |
|  | Steareth-21 (Brij 721) | 0.37 |
|  | Steareth-2 (Brij 72) | 1.10 |
|  | Distearyldimonium chloride (Varisoft TA-100) | 0.95 |
|  | Propyl Paraben | 0.10 |
|  | Polypropylene glycol- 15 stearyl ether (Arlamol E) | 3.25 |
| PHASE C: | Polypropylene glycol-15 stearyl ether (Arlamol E) | 2.17 |
|  | titanium dioxide | 0.75 |
| PHASE D: | Niacinamide | 5.00 |
|  | Citric acid | 0.19 |
|  | water U.S.P. | 17.00 |
|  | 50% NaOH | 0.94 |
| PHASE E: | Benzyl Alcohol | 0.50 |
|  | Silicone fluid (DC Q2 - 1401; cyclomethicone/dimethiconol - 5%o blend | 0.75 |
|  | dimethicone 10 cst | 1.00 |
|  | polyethylene Low Density Beads | 1.00 |
| PHASE F: | Fragrance | 0.10 |
| PHASE G: | 50% NaOH | 0.33 |

Blend the A phase components with a suitable mixer (e.g., Tekmar model RW20DZM), heating while stirring to a temperature of 70–80° C. Separately, blend the B phase components with a suitable mixer and heat with mixing to melt the components. Separately, blend the C phase components and mil to obtain an acceptably smooth mixture (e.g., using a Tekmar T50 Mill).

Add the C phase mixture to the B phase mixture and mix. Then add the resulting mix to the A phase mixture with mixing, cool with a cold water bath and mill, then continue stirring. Remove the combination from the bath, with continued stirring, once the temperature reaches 40° C.

Separately, blend the D phase components by stirring until dissolved, then add this to the combination of A–C materials.

Separately, blend the E phase components by mixing until smooth and continuous, then add this to the combination of the A–D materials. Add and mix the fragrance, then the NaOH. Adjust the pH as necessary to 5.5.

Apply the composition to a subject's wrinkled, aged, or photodamaged facial skin at the rate of 2 mg composition/cm$^2$ skin once or twice daily for a period of at least 3–6 months to reduce fine lines and wrinkles and improve skin surface texture.

Example 2

An emulsion is prepared by conventional methods from the following components:

| Ingredient | Weight % |
|---|---|
| Silicone fluid (Dow Corning DC 345) | 15.0 |
| Silicone fluid (Dow Corning DC 3225C) | 2.5 |
| Silicone fluid (Goldschmidt Abil We09) | 2.5 |
| Water | 71.4 |
| Niacinamide | 5.0 |
| Tetrasodium EDTA | 0.1 |
| Benzyl alcohol | 0.3 |
| Methyl paraben | 0.2 |
| Glycerin | 3.0 |

Form the water phase in a suitable vessel charged with the water as follows: add the glycerin and then niacinamide to the water with stirring. Add to this mixture with stirring the methyl paraben dissolved in the benzyl alcohol. Add to this mixture with stirring the EDTA.

Form the silicone phase in a separate suitable vessel by adding and stirring together the silicone fluids.

Add the water phase to the silicone phase slowly with stirring to form the emulsion.

Apply the resulting composition to a subjects wrinkled, aged, or photodamaged facial skin at the rate of 2 mg composition/cm$^2$ skin once or twice daily for a period of at least 3–6 months to reduce fine lines and wrinkles and improve skin surface texture.

Example 3

A skin cream is prepared by conventional methods from the following components.

|  | Ingredient (CTFA Name) | Weight % |
|---|---|---|
| PHASE A: | Water U.S.P. | 63.96 |
|  | Disodium EDTA | 0.15 |
|  | Glycerin | 5 |
| PHASE B: | Cetyl hydroxy ethyl cellulose | 0.15 |
|  | Methyl Paraben | 0.25 |
| PHASE C: | Cetyl Alcohol | 0.5 |
|  | Stearyl Alcohol | 0.5 |
|  | Behenyl Alcohol | 0.5 |
|  | Cetyl ricinoleate | 3 |
|  | Steareth-2 (Brij 72) | 1.05 |
|  | Distearyldimonium chloride (Varisoft TA-100) | 0.25 |
|  | Propyl Paraben | 0.10 |
|  | Myristyl myristate | 1.5 |
|  | Caprylic/Capritryglycerides | 1.5 |
|  | Mineral Oil | 2 |
|  | Fatty acid ester of sugar* | 1 |
|  | Polypropylene glycol-15 stearyl ether (Arlamol E) | 1.05 |
| PHASE D: | dimethicone 10 cst (Dow Corning) | 2 |
| PHASE E: | Niacinamide | 5 |
|  | Water U.S.P. | 10 |
| PHASE F: | Benzyl Alcohol | 0.5 |
| PHASE G | 50% NaOH | 0.04 |

*A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty moieties and about 1 oleic acid moiety in the molecule, e.g., sucrose ester of cottonseed oil fatty acids.

Blend the A phase components with a suitable mixer (e.g., Tekmar model RW20DZM), heating while stirring to a temperature of about 70–80° C. Add the cetyl hyroxy ethyl cellulose and methyl paraben with mixing at about 70–80° C. to melt the components. Separately, blend the C phase components and mill to obtain an acceptably smooth mixture (e.g., using a Tekmar T50 Mill).

Add the C phase mixture to the above mixture and mix. Remove the combination from the bath, with continued stirring, once the temperature reaches about 45° C. Add the dimethicone and mix.

Separately, blend the E phase components by mixing until smooth and continuous, then add this to the above mixture. Add and mix in the benzyl alcohol, then the NaOH. Adjust the pH as necessary to 7.

Apply the composition to a subject's wrinkled, aged, or photodamaged facial skin at the rate of 2 mg composition/cm$^2$ skin once or twice daily for a period of at least 3–6 months to reduce fine lines and wrinkles and improve skin surface texture.

Example 4

A skin cream is prepared by conventional methods from the following components.

|  | Component | Weight % |
|---|---|---|
| PHASE A: | benzyl alcohol | 0.30 |
|  | methyl p-hydroxybenzoate (a.k.a. methylparaben) | 0.20 |
|  | ethanol | 3.00 |
| PHASE B: | Water | 60.60–61.35 |
|  | disodium EDTA | 0.50 |
|  | glycerol | 10.00 |
|  | hexylene glycol | 2.00 |
|  | niacinamide | 2.00 |
|  | triethanol amine | 0.05 |
|  | butylated hydroxytoluene | 0.10 |
| PHASE C: | Dow Corning 345 Fluid | 12.50 |
|  | Abil WE-09 | 2.50 |
|  | Dow Corning-3225C | 2.50 |
|  | petrolatum | 1.50 |
|  | retinol (10% in soybean oil) | 0.75–1.50 |
|  | fatty acid ester of sugar* | 1.00 |

*See Example 3

Blend the A phase components with a suitable mixer (e.g., Tekmar model RW20DZM). Blend the B phase components into the A phase with a suitable mixer. Separately, blend the C phase components until they are uniform. Add the C phase mixture to the A/B phase mixture, mix until uniform and emulsified, and then mill to obtain an acceptably smooth mixture (e.g., using a Tekmar T50 Mill).

Apply the composition to a subject's wrinkled, intrinsically aged, or photodamaged facial skin at the rate of 2 mg composition/cm$^2$ skin once or twice daily for a period of at least 3–6 months to improve skin surface texture, including diminishing fine lines and wrinkles.

An alternative skin cream having reduced retinol levels can be prepared in the same manner from the above components wherein the retinol is added in an amount of 0.025% (0.25% of 10% retinol in soybean oil), quo sine to 100% with water, the amounts of the other components being as shown.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method of regulating mammalian skin pore size, comprising applying to the skin of a mammal a safe and effective amount of a composition comprising:

(a) a safe and effective amount of a vitamin $B_3$ compound selected from the group consisting of niacinamide, tocopherol nicotinate, and combinations thereof; and (b) a carrier for said vitamin $B_3$ compound.

2. The method of claim 1 wherein said vitamin $B_3$ compound is niacinamide.

3. A method of regulating mammalian skin pore size, comprising applying to the skin of a mammal a safe and effective amount of a composition comprising:

(a) a safe and effective amount of a vitamin $B_3$ compound selected from the group consisting of niacinamide, tocopherol nicotinate, and combinations thereof;

(b) a second active selected from the group consisting of salicylic acid; desquamatory agents selected from the group consisting of zwitterionic surfactants; antioxidants selected from the group consisting of esters of tocopherol; sunscreens selected from the group consisting of zinc oxide, titanium dioxide, 4,4'-t-butyl methoxydibenzoyl-methane, 2-ethylhexyl-p-methoxycinnamate, phenyl benzimidazole sulfonic acid, octocrylene and combinations thereof; retinoids selected from the group consisting of retinol, retinol esters, retinal, retinoic acid, tocopheryl-retinoate, adapalene, tazarotene and combinations thereof; and (c) a carrier for said vitamin $B_3$ compound.

4. The method of claim 3 wherein said retinoid is selected from the group consisting of retinol, retinyl palmitate, retinyl acetate, retinyl proprionate, retinal and combinations thereof.

5. The method of claim 4 wherein said retinoid is selected from the group consisting of retinol, retinyl palmitate, and combinations thereof.

* * * * *

UNITED STATES PATENT AND TRADEMARK OFFICE
CERTIFICATE OF CORRECTION

PATENT NO. : 5,939,082
DATED : August 17, 1999
INVENTOR(S) : John Erich Oblong, et al It is certified that error appears in the above-identified patent and that said Letters Patent is hereby corrected as shown below:

At column 9, line 17 "$R_3SiO[R_2SiO]_{xp}SiR_3$" should read --$R_3SiO[R_2SiO]_xSiR_3$--.

At column 12, line 42 "*Toiletries* vol." should read --*Toiletries*, vol.--.

At column 17, lines 58-59 "*Cosmetics Science*" should read --*Cosmetics, Science*--.

At column 19, line 61 "*Technology* 1st" should read --*Technology*, 1st--.

At column 21, lines 10-11 "*Pharmacology* 1" should read --*Pharmacology*, 1--.

At column 23, line 42 "Sunscreens" should read --E. Sunscreens--.

At column 24, line 20 "2-hydroxy4" should read --2-hydroxy-4--.

At column 24, line 22 "ethyl4-(bis" should read --ethyl-4-(bis--.

At column 24, line 27 "arinobenzoate" should read --aminobenzoate--.

At column 24, line 34 "2-hydroxy4" should read --2-hydroxy-4--.

At column 24, line 54 "2-hydroxy4" should read --2-hydroxy-4--.

At column 24, line 57 "ethylhexyl)4-aminobenzoic" should read --ethylhexyl)-4-aminobenzoic--.

At column 24, line 57 "2-hydroxy4" should read --2-hydroxy-4--.

At column 31, line 47 "mil to" should read --mill to--.

UNITED STATES PATENT AND TRADEMARK OFFICE
CERTIFICATE OF CORRECTION

PATENT NO. : 5,939,082
DATED : August 17, 1999
INVENTOR(S) : John Erich Oblong, et al It is certified that error appears in the above-identified patent and that said Letters Patent is hereby corrected as shown below:

At column 32, line 26 "subjects" should read --subject's--.

At column 32, line 63 "fatty moieties" should read --fatty acid moieties--.

Signed and Sealed this

First Day of February, 2000

Attest:

Attesting Officer

Q. TODD DICKINSON

Acting Commissioner of Patents and Trademarks